United States Patent
Shan et al.

(10) Patent No.: US 9,663,451 B2
(45) Date of Patent: May 30, 2017

(54) FORMS OF CO-CRYSTALS OF AGOMELATINE AND P TOLUENESULPHONIC ACID, A PROCESS FOR THEIR PREPARATION AND PHARMACEUTICAL COMPOSITIONS CONTAINING THEM

(71) Applicants: LES LABORATOIRES SERVIER, Suresnes (FR); SHANGHAI INSTITUTE OF PHARMACEUTICAL INDUSTRY, Shanghai (CN)

(72) Inventors: Hanbin Shan, Gaoan (CN); Yuhui Shen, Shanghai (CN); Ying Luo, NanChang (CN); Philippe Letellier, Orléans (FR); Michael Lynch, Saint Jean de la Ruelle (FR)

(73) Assignees: LES LABORATOIRES SERVIER, Suresnes (FR); SHANGHAI INSTITUTE OF PHARMACEUTICAL INDUSTRY, Jing'an District, Shanghai (CN)

(*) Notice: Subject to any disclaimer, the term of this patent is extended or adjusted under 35 U.S.C. 154(b) by 0 days.

(21) Appl. No.: 14/908,253

(22) PCT Filed: Jul. 30, 2014

(86) PCT No.: PCT/FR2014/051972
§ 371 (c)(1),
(2) Date: Jan. 28, 2016

(87) PCT Pub. No.: WO2015/015118
PCT Pub. Date: Feb. 5, 2015

(65) Prior Publication Data
US 2016/0168077 A1 Jun. 16, 2016

(30) Foreign Application Priority Data

Jul. 31, 2013 (CN) .................. PCT/CN2013/080472
Oct. 17, 2013 (FR) ..................................... 13/60121

(51) Int. Cl.
*C07C 233/18* (2006.01)
*C07C 309/30* (2006.01)
*C07C 303/32* (2006.01)
*C07C 231/22* (2006.01)

(52) U.S. Cl.
CPC .......... *C07C 233/18* (2013.01); *C07C 231/22* (2013.01); *C07C 303/32* (2013.01); *C07C 309/30* (2013.01); *C07B 2200/13* (2013.01)

(58) Field of Classification Search
CPC ... C07C 233/18; C07C 309/30; C07C 303/32; C07C 231/22
See application file for complete search history.

(56) References Cited

U.S. PATENT DOCUMENTS 7,498,466 B2 * 3/2009 Souvie .................. C07C 233/18
564/172
2015/0141519 A1 5/2015 Wang et al.

FOREIGN PATENT DOCUMENTS

CN          102702041        10/2012

OTHER PUBLICATIONS

International Search Report for International Application No. PCT/FR2014/051972, dated Feb. 16, 2015.
Written Opinion for French Application No. FR1360121 dated Oct. 17, 2013.
Written Opinion for International Application No. PCT/FR2014/051972, dated Feb. 16, 2015.

* cited by examiner

*Primary Examiner* — Shirley V Gembeh
(74) *Attorney, Agent, or Firm* — Hueschen and Sage

(57) ABSTRACT

The present invention relates to new forms of co-crystals of agomelatine and p-toluenesulphonic acid, to a process for their preparation and to pharmaceutical compositions containing them. The co-crystals according to the invention have better solubility than agomelatine and are therefore more suitable for the preparation of pharmaceutical compositions. They also have better stability and purity and, moreover, are obtained by a simple process which does not include any difficult steps.

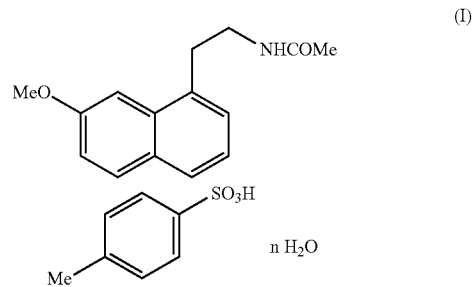

8 Claims, 2 Drawing Sheets

FORMS OF CO-CRYSTALS OF AGOMELATINE AND P TOLUENESULPHONIC ACID, A PROCESS FOR THEIR PREPARATION AND PHARMACEUTICAL COMPOSITIONS CONTAINING THEM

The present invention relates to new forms of co-crystals of agomelatine and p-toluenesulphonic acid, to a process for their preparation, and to pharmaceutical compositions containing them.

Agomelatine, or N-[2-(7-methoxy-1-naphthyl)ethyl]acetamide, has the structure of formula (II):

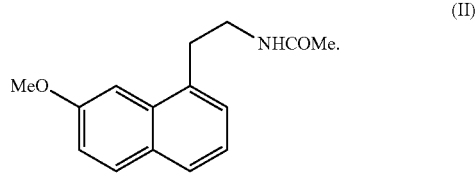

Agomelatine is marketed by the French company Servier under the trade name Valdoxan® or Thymanax® as an agonist of receptors of the melatoninergic system and an antagonist of the 5-$HT_{2C}$ receptor. It is the first antidepressant of the melatoninergic type, for use in the treatment of major depression, improving sleep and sexual function.

Agomelatine, its preparation and its use in therapeutics have been described in European patents EP 0 447 285 and EP 1 564 202.

In view of its pharmaceutical value, it is important to be able to produce agomelatine or a complex thereof with improved purity, solubility and reproducibility.

A process for the preparation of the agomelatine/p-toluenesulphonic acid co-crystal has been reported in patent application CN102702041, in which the structure of the co-crystal was identified by $^1$H-NMR, the product obtained being amorphous.

The amorphous form has a number of disadvantages as a pharmaceutical product, such as adherence to walls, poor flow properties, low stability, and it is accordingly still valuable to have available a well defined crystalline form of a chemical entity.

The object of the present invention is to prepare new crystalline forms of co-crystals of agomelatine and p-toluenesulphonic acid which have excellent properties in terms of solubility, stability and purity, allowing their use in the manufacture of pharmaceutical compositions comprising agomelatine to be envisaged.

The present invention relates to crystalline forms of co-crystals of agomelatine and p-toluenesulphonic acid having the structure of formula (I):

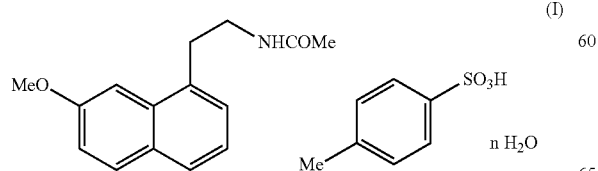

wherein n represents 0 or 1.

The preferred compounds according to the invention are the following co-crystals of agomelatine and p-toluenesulphonic acid:

agomelatine/p-toluenesulphonic acid (1/1) monohydrate co-crystal,
agomelatine/p-toluenesulphonic acid (1/1) co-crystal.

Figure 1:
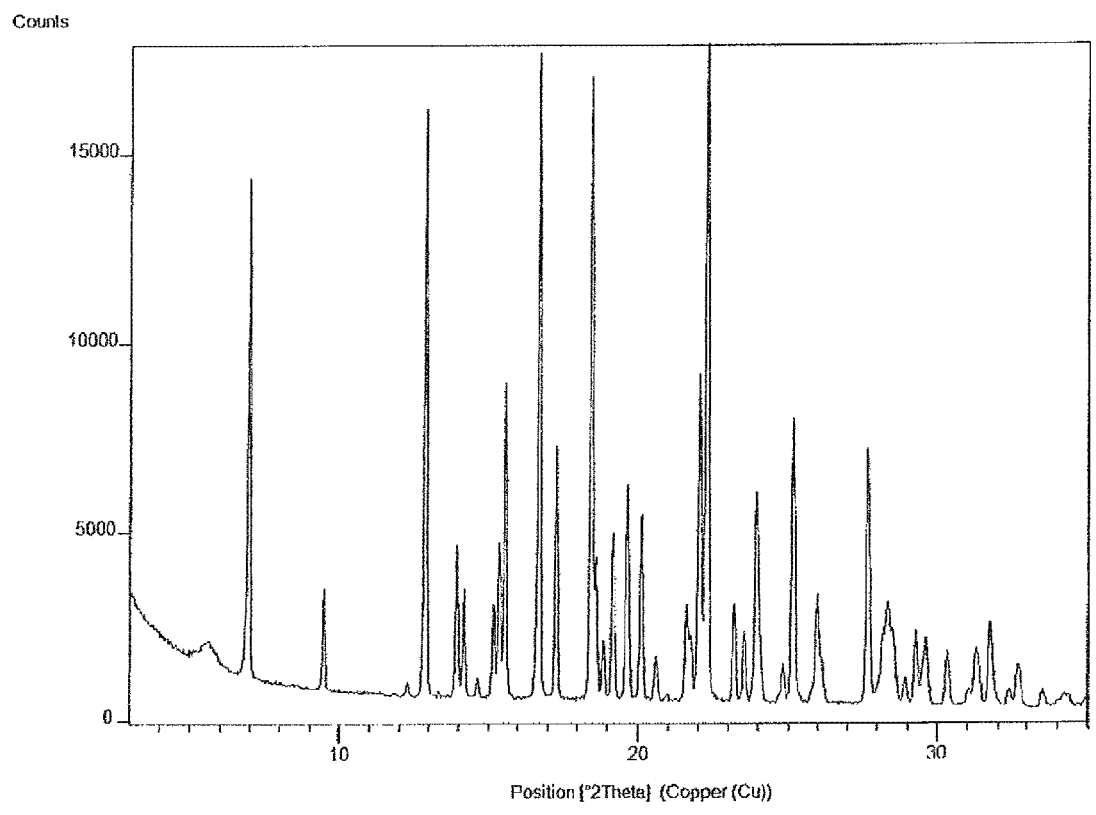

The agomelatine/p-toluenesulphonic acid (1/1) monohydrate co-crystal is characterised by its X-ray powder diffraction diagram shown in FIG. 1, measured using a Panalytical Xpert Pro MPD diffractometer (copper anticathode). The principal lines are expressed in terms of interplanar distance d, Bragg's angle 2 theta (expressed in °±0.2), and relative intensity (expressed as a percentage relative to the most intense line) and are listed in Table 1:

TABLE 1

Table of the diffraction peaks of the agomelatine/p-toluenesulphonic acid (1/1) monohydrate co-crystal

| 2-Theta (°) exp. | d (Å) exp. | Intensity (%) |
|---|---|---|
| 6.9631 | 12.6846 | 77.52 |
| 9.4831 | 9.31871 | 16.21 |
| 12.8823 | 6.86648 | 100 |
| 13.9527 | 6.34201 | 23.16 |
| 14.1761 | 6.24258 | 16.06 |
| 15.1817 | 5.83128 | 13.38 |
| 15.379 | 5.75689 | 25 |
| 15.5788 | 5.68351 | 46.24 |
| 16.7156 | 5.29947 | 94.46 |
| 17.2926 | 5.12391 | 37.98 |
| 18.4671 | 4.80058 | 92.47 |
| 18.6356 | 4.75756 | 22.34 |
| 19.199 | 4.6192 | 25.69 |
| 19.6747 | 4.50857 | 35.74 |
| 20.1398 | 4.4055 | 28.53 |
| 21.6248 | 4.1062 | 14.93 |
| 22.0586 | 4.02643 | 52.23 |
| 22.2859 | 3.98587 | 99.09 |
| 23.2175 | 3.82799 | 15.22 |
| 23.9607 | 3.71092 | 32.37 |
| 25.1733 | 3.53485 | 42.09 |
| 26.0152 | 3.42233 | 16.64 |
| 27.7148 | 3.2162 | 39.29 |
| 28.23 | 3.15866 | 11.25 |
| 28.4033 | 3.13979 | 16.33 |

When the co-crystal of the present invention is characterised by X-ray diffraction measurement, there may be errors of measurement of the identified peaks which are sometimes attributable to the equipment or to the conditions used. More especially, the 2 theta values can have an error of approximately ±0.2 and sometimes an error of approximately ±0.1, even if sophisticated equipment is used. The measurement error must accordingly be taken into account when identifying the structure of the co-crystal.

The crystalline structure of the agomelatine/p-toluenesulphonic acid (1/1) monohydrate co-crystal was determined and the following parameters were identified:

Space group: P 21 21 21 (19)
Lattice parameters: a=13.7359(3) Å, b=25.3716(6) Å, c=6.4487(1) Å; α=90°, β=90(2°), γ=90°
Volume of the lattice: $V_{unit\ cell}$=2247.4 Å$^3$ The agomelatine/p-toluenesulphonic acid (1/1) monohydrate co-crystal is also characterised by DSC (differential scanning calorimetry) in the spectrum shown in FIG. 2, which shows a broad endotherm corresponding to the dehydration of the co-crystal and the melting thereof at a temperature of approximately 78° C. (and a temperature peak at approximately 87° C.).

Figure 3:
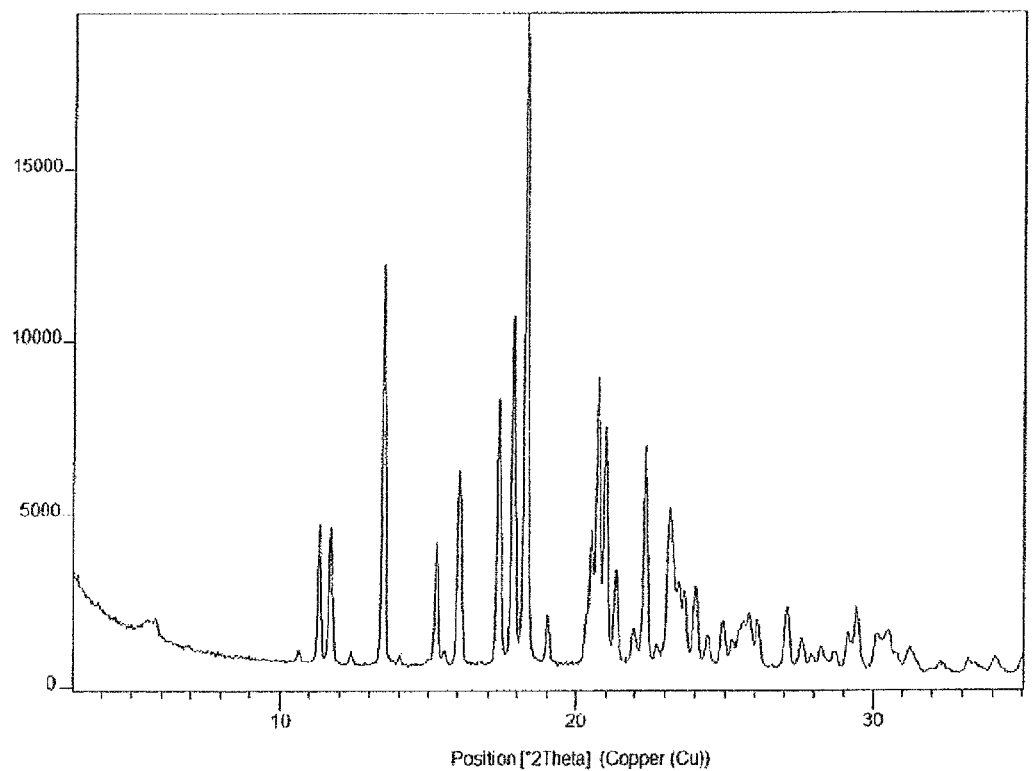

The invention relates also to the agomelatine/p-toluenesulphonic acid (1/1) co-crystal which is characterised by its X-ray powder diffraction diagram shown in FIG. 3, measured using a Panalytical Xpert Pro MPD diffractometer (copper anticathode). The principal lines are expressed in terms of interplanar distance d, Bragg's angle 2 theta (expressed in °+0.2), and relative intensity (expressed as a percentage relative to the most intense line) and are listed in Table 2:

TABLE 2

Table of the diffraction peaks of the agomelatine/p-toluenesulphonic acid (1/1) co-crystal

| 2-Theta (°) exp. | d (Å) exp. | Intensity (%) |
| --- | --- | --- |
| 11.2964 | 7.82664 | 21.53 |
| 11.6596 | 7.58367 | 20.45 |
| 13.4436 | 6.58103 | 61.31 |
| 15.2416 | 5.80848 | 18.42 |
| 16.0185 | 5.52847 | 30.89 |
| 17.3473 | 5.10789 | 41.39 |
| 17.8289 | 4.97096 | 54.3 |
| 18.2535 | 4.85629 | 100 |
| 20.4891 | 4.33118 | 19.84 |
| 20.6912 | 4.28932 | 45.12 |
| 20.9516 | 4.23659 | 36.73 |
| 21.3088 | 4.16638 | 14.93 |
| 22.2998 | 3.98342 | 33.92 |
| 23.129 | 3.84244 | 24.66 |
| 23.4107 | 3.79685 | 12.89 |
| 23.6474 | 3.75938 | 12.34 |
| 23.9983 | 3.7052 | 12.8 |

When the co-crystal of the present invention is characterised by X-ray diffraction measurement, there may be errors of measurement of the identified peaks which are sometimes attributable to the equipment or to the conditions used. More especially, the 2 theta values can have an error of approximately ±0.2 and sometimes an error of approximately ±0.1, even if sophisticated equipment is used. The measurement error must accordingly be taken into account when identifying the structure of the co-crystal.

The crystalline structure of the agomelatine/p-toluenesulphonic acid (1/1) co-crystal was determined and the following parameters were identified:

Space group: P $2_1 2_1 2_1$ (19)

Lattice parameters: a=8.6683(3) Å, b=30.360(1) Å, c=8.0982(4) Å; α=90°, β=90°, γ=90°

Volume of the lattice: $V_{unit\ cell}$=2131.2 Å$^3$

Figure 4:
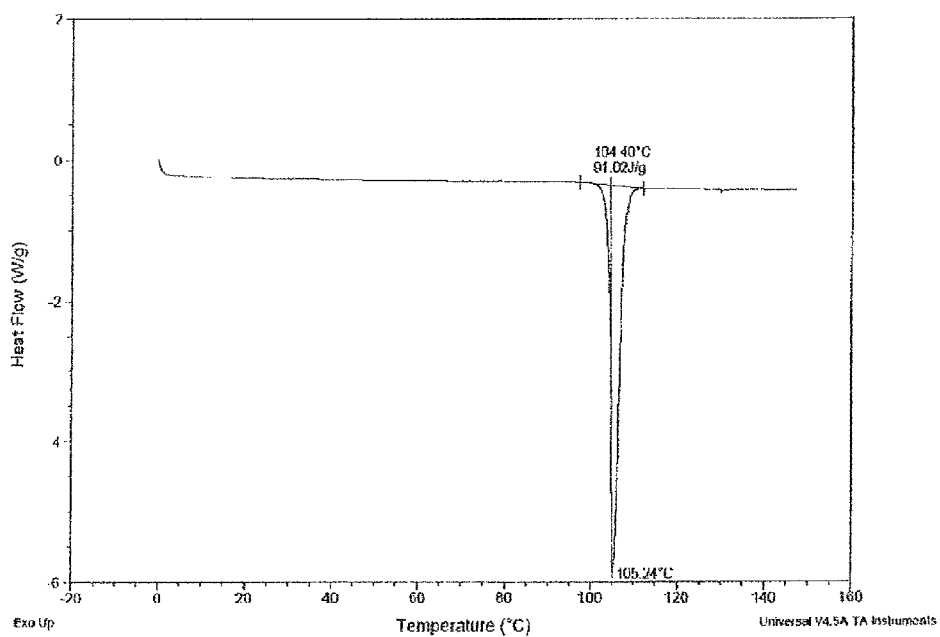

The agomelatine/p-toluenesulphonic acid (1/1) co-crystal is also characterised by DSC (differential scanning calorimetry) in the spectrum shown in FIG. 4, which shows an endotherm corresponding to the melting of the complex at a temperature of approximately 105° C.

The invention relates also to a process for obtaining co-crystals of agomelatine and p-toluenesulphonic acid, wherein:

agomelatine and p-toluenesulphonic acid monohydrate are mixed in an organic or aqueous-organic solvent in the desired proportions;

the solution obtained is stirred and optionally heated at a temperature not greater than the boiling point of the chosen solvent;

the mixture is cooled, with stirring, and the complex precipitates naturally or precipitates after being taken up in a second solvent;

the precipitate obtained is filtered and dried;

optionally, the precipitate is dried by heating.

In the process according to the invention, the solvent used is preferably an ether such as, for example, diisopropyl ether, tetrahydrofuran, dioxane or methyl tert-butyl ether; or an aromatic hydrocarbon such as, for example, toluene. When a second solvent is used in order to promote precipitation of the complex, the solvent chosen is an alcohol such as, for example, methanol, ethanol or tert-butanol; an alkane such as, for example, n-hexane or n-heptane; or benzonitrile.

An alternative process comprises co-grinding the two constituents of the co-crystal. The co-grinding is preferably carried out in a steel jar. A variant of this process comprises adding an organic solvent during the grinding; in this case, the co-crystal obtained is then dried. Among the solvents used, there may be mentioned, more especially, ethers such as, for example, diisopropyl ether, or methyl tert-butyl ether. Alcohols such as, for example, methanol or tert-butanol can also be used.

The grinding is advantageously carried out using non-oxidisable balls. The grinding is carried out using vibrations, preferably vibrations with a frequency ranging from 20 to 30 Hz. The vibrations are applied for a period which may range from 5 minutes to 3 hours.

Another alternative process comprises mixing two solutions containing each of the constituents and rapidly freezing the mixture obtained at a very low temperature, and then at that same very low temperature drying the co-crystal thereby obtained. The two constituents are advantageously mixed in an organic or aqueous-organic solvent. The freezing and drying are carried out preferably between −40° C. and −60° C., and more preferably at −40° C.

Another advantageous process according to the invention comprises mixing the powders of agomelatine and of the acid in question in a mixer and then extruding the mixture by twin-screw extrusion without a die in order to obtain a solid grain directly at the outlet of the extruder. The screw profile used is preferably a high-shear profile, optionally with the use of kneader elements allowing the contact surface between the constituents to be improved. The L/D parameter of the screw may vary between 10 and 40 and the speed of rotation between 10 and 200 rpm. The temperature used varies from 40 to 100° C.

The co-crystals of agomelatine and p-toluenesulphonic acid that are obtained have a solubility that is increased very significantly relative to agomelatine per se, which renders them more suitable for the preparation of pharmaceutical formulations. The co-crystals of agomelatine and p-toluenesulphonic acid according to the invention additionally exhibit advantageous properties of stability, purity and solubility. They are, moreover, obtained by a simple process which does not include any difficult steps.

The pharmacological studies of the co-crystals according to the invention show that they can be used for the treatment of disorders of the melatoninergic system and, more especially, in the treatment of stress, sleep disorders, anxiety disorders and especially generalised anxiety disorder, obsessive compulsive disorders, mood disorders and especially bipolar disorders, major depression, seasonal affective disorder, cardiovascular pathologies, pathologies of the digestive system, insomnia and fatigue due to jet-lag, schizophrenia, panic attacks, melancholia, appetite disorders, obesity, insomnia, pain, psychotic disorders, epilepsy, diabetes, Parkinson's disease, senile dementia, various disorders associated with normal or pathological ageing, migraine, memory loss, Alzheimer's disease, and also in cerebral circulation disorders. In another field of activity, it will be possible to use the co-crystals according to the invention in sexual dysfunctions, as ovulation inhibitors and immunomodulators and in the treatment of cancers.

The invention relates also to pharmaceutical compositions comprising as active ingredient a co-crystal of agomelatine and p-toluenesulphonic acid according to the invention together with one or more adjuvants or excipients.

Among the pharmaceutical compositions according to the invention there may be mentioned, more especially, those that are suitable for oral, parenteral (intravenous or subcutaneous) or nasal administration, tablets or dragées, granules, sublingual tablets, capsules, lozenges, suppositories, creams, ointments, dermal gels, injectable preparations, drinkable suspensions and chewing gums.

The useful dosage can be varied according to the nature and severity of the disorder, the administration route and the age and weight of the patient. The dosage varies from 0.1 mg to 1 g of agomelatine per day in one or more administrations.

Representative examples of the present invention are illustrated with the corresponding figures in order better to evaluate the subject-matter, features and advantages thereof.

FIG. 1: X-ray powder diffraction diagram of the agomelatine/p-toluenesulphonic acid (1/1) monohydrate co-crystal.

Figure 2:
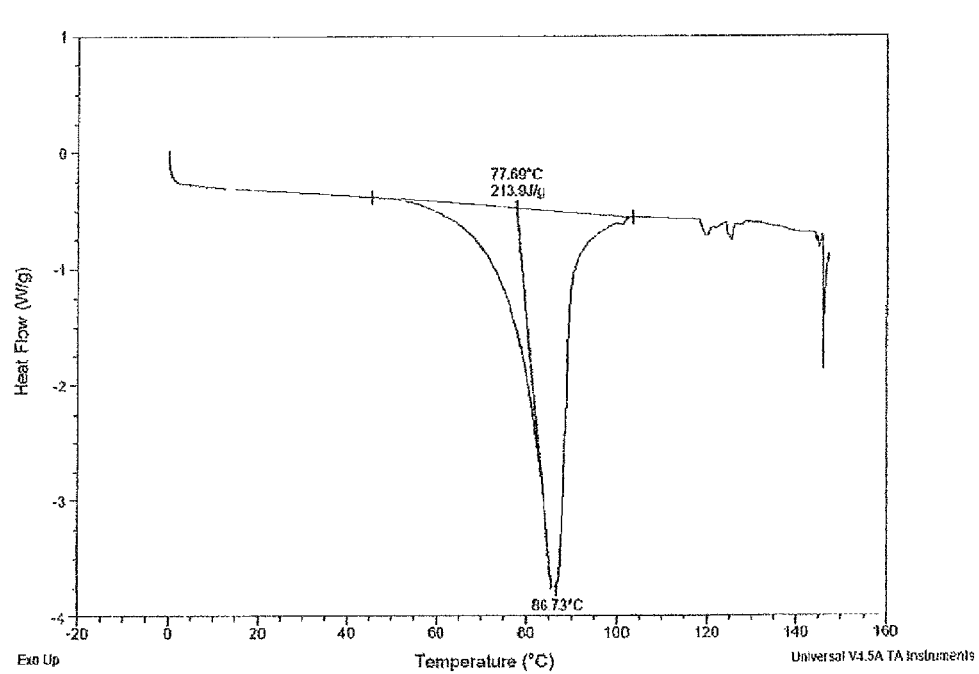

FIG. 2: DSC thermogram of the agomelatine/p-toluenesulphonic acid (1/1) monohydrate co-crystal.

FIG. 3: X-ray powder diffraction diagram of the agomelatine/p-toluenesulphonic acid (1/1) co-crystal.

FIG. 4: DSC thermogram of the agomelatine/p-toluenesulphonic acid (1/1) co-crystal.

EXAMPLE 1

Agomelatine/p-Toluenesulphonic Acid (1/1) Monohydrate Co-Crystal

Procedure 1

Agomelatine (5.00 g, 1 eq.) and p-toluenesulphonic acid monohydrate (3.92 g, 1 eq.) are placed in a reactor. 40 ml of tetrahydrofuran and 20 ml of hexane are added. The suspension is stirred under reflux for 0.5 hour until it becomes cloudy (if it does not become cloudy, further tetrahydrofuran is added until it is cloudy). The solution is cooled naturally to 5° C. and stirred for 0.5 hour, and then the suspension is filtered. The cake is dried for one hour in vacuo. 8.53 g of a white solid are obtained.

Yield: 95.8%

Melting point: 78° C.

Procedure 2

Agomelatine (5.00 g, 1 eq.) and p-toluenesulphonic acid monohydrate (3.952 g, 1 eq.) are introduced into a reactor. 40 ml of acetone and 10 ml of hexane are added. The suspension is stirred under reflux for 0.5 hour until it becomes cloudy (if it does not become cloudy, further acetone is added until it is cloudy). The solution is cooled naturally to 5° C. and stirred for 0.5 hour, and the suspension is then filtered. The cake is dried for one hour in vacuo. 8.06 g of a white solid are obtained.

Yield: 90.4%

Melting point: 78° C.

Procedure 3

Agomelatine (0.5 g) and p-toluenesulphonic acid monohydrate (0.392) are placed in a 50-ml non-oxidisable jar. Two stainless steel balls of 12 mm diameter are added and the jar is closed. Vibrations with a frequency of 30 Hz are applied for 15 minutes to yield, after drying overnight at ambient temperature, 0.881 g of solid.

Melting point: 78° C.

Procedure 4

Agomelatine (0.5 g) and p-toluenesulphonic acid monohydrate (0.392) are placed in a 50-ml non-oxidisable jar. Two stainless steel balls of 12 mm diameter are added and the jar is closed. 100 μl of methyl tert-butyl ether are added. Vibrations with a frequency of 30 Hz are applied for 30 minutes to yield, after drying overnight at ambient temperature, 0.883 g of solid.

Melting point: 78° C.

Procedure 5

Agomelatine (5 g) and p-toluenesulphonic acid monohydrate (3.92 g) are placed in a 100-ml non-oxidisable jar. Two stainless steel balls of 12 mm diameter are added and the jar is closed. 100 μl of methyl tert-butyl ether are added. Vibrations with a frequency of 30 Hz are applied for 30 minutes to yield, after drying overnight at ambient temperature, 8.83 g of solid.

Melting point: 78° C.

EXAMPLE 2

Agomelatine/p-Toluenesulphonic Acid (1/1) Co-Crystal 2 g of the agomelatine/p-toluenesulphonic acid (1/1) monohydrate co-crystal obtained in Example 1 are heated at 85° C. for 4 hours. A white solid is obtained.

Yield: 100%

Melting point: 105° C.

In the examples below it is possible to use commercially available agomelatine or agomelatine prepared by one of the methods described in the prior art.

EXAMPLE 3

Pharmaceutical Compositions: Capsules Containing a Dose of 25 mg of Agomelatine

| Formulation for the preparation of 1000 capsules each containing 25 mg of agomelatine | |
|---|---|
| Compound of Example 1 | 44.5 g |
| Lactose (Spherolac 100) | 85.2 g |
| Starch 1500 | 25.5 g |
| CMS-Na | 8.5 g |
| Ac-Di-Sol ® (FMC) | 17 g |
| Stearic acid | 3.4 g |

| Formulation for the preparation of 1000 capsules each containing 25 mg of agomelatine | |
|---|---|
| Compound of Example 2 | 42.7 g |
| Lactose (Spherolac 100) | 85.2 g |
| Starch 1500 | 25.5 g |
| CMS-Na | 8.5 g |
| Ac-Di-Sol ® (FMC) | 17 g |
| Stearic acid | 3.4 g |

EXAMPLE 4

Pharmaceutical Compositions: Tablets Each Containing a Dose of 25 mg of Agomelatine Formulation for the preparation of 1000 tablets each containing 25 mg of agomelatine:

Compound of Example 1 . . . 44.5 g

Lactose monohydrate . . . 115 g

Magnesium stearate . . . 2 g

Maize starch . . . 33 g
Maltodextrins . . . 15 g
Anhydrous colloidal silica . . . 1 g
Pregelatinised maize starch, Type A . . . 9 g Formulation for the preparation of 1000 tablets each containing 25 mg of agomelatine:
Compound of Example 2 . . . 42.7 g
Lactose monohydrate . . . 115 g
Magnesium stearate . . . 2 g
Maize starch . . . 33 g
Maltodextrins . . . 15 g
Anhydrous colloidal silica . . . 1 g
Pregelatinised maize starch, Type A . . . 9 g
Detection Methods and Results
1. Purity of the Samples Chromatography conditions: C18 column; mobile phase: phosphate buffer 10 mmol/L (adjusted to pH 7.0 with NaOH): acetonitrile 2:7 (v/v); temperature of the column: 40° C.; detection wavelength: 220 nm; internal standard method used with the compound of Examples 1 and 2.

1 mg/ml solutions of the compounds of the invention are prepared with the mobile phase. 10 µl of each solution are injected into the liquid chromatography system and the chromatograms are recorded.

The compounds of Examples 1 and 2 have purities greater than or equal to 99%.

2. Stability

Samples of the compounds of Examples 1 and 2 are placed in incubators at 40° C. for 30 days in order to determine their stability by HPLC. The results are presented in Table 3:

TABLE 3

|  | 25° C., 60% RH OB | 40° C., 75% RH OB | 50° C. CB | 70° C. CB |
|---|---|---|---|---|
| Compound of Example 1 | Stable | Stable | Stable | Stable |
| Compound of Example 2 | Changes into the monohydrate | Changes into the monohydrate | Changes into the monohydrate | Stable |

RH: relative humidity;
OB: open bottle;
CB: closed bottle

3. Solubility in Water

By means of an external standard method, the compounds of Examples 1 and 2 are tested by HPLC and compared with agomelatine of form II. The results are presented in Table 4 in the form of % increase in solubility relative to the solubility of agomelatine of form II:

TABLE 4

| | Solubility (increase versus agomelatine form II) | | |
|---|---|---|---|
| Sample | in water | in 0.1N HCl | in a buffer pH 6.8 |
| Compound of Example 1 | +41% | +50% | +49% |
| Compound of Example 2 | +35% | +45% | +60% |

The results show that the co-crystals of agomelatine and p-toluenesulphonic acid of the present invention have greater solubility than agomelatine of form II per se in water, in 0.1N HCl, which is similar to human gastric fluids, or in a buffer at pH 6.8. These results show that the co-crystals have a far better potential in terms of bioavailability than agomelatine of form II.

4. DSC Analyses

Approximately 5-10 mg of the compounds of Examples 1 and 2 are weighed into an aluminium crucible closed with a pierced (non-hermetic) aluminium lid, unless specified otherwise. The sample is introduced into a TA Q1000 device (equipped with a cooler), cooled and maintained at 25° C. After thermal stabilisation, the sample and the reference are heated from 200° C. to 250° C. at a rate of 10° C./min and the response to the heat flow is recorded. Nitrogen is used as the purge gas, at a flow rate of 100 cm$^3$/min.

The DSC thermograms obtained with the compounds of Examples 1 and 2 are shown in FIGS. 2 and 4.

5. Analysis of the Crystalline Structure

The conditions of measurement of the X-ray powder diffraction diagrams of the products of Examples 1 and 2 are as follows:

Approximately 50 mg of the compounds of Examples 1 and 2 are placed between two Kapton® films and fixed to the sample support. The sample is then placed in a PANALYTICAL XPERT-PRO MPD diffractometer in transmission mode under the following conditions:
Parameters of the generator: 45 kV/40 mA
Configuration theta/theta
Anode: Cu
K-Alpha1 [Å] 1.54060
K-Alpha2 [Å] 1.54443
K-Beta [Å] 1.39225
K-A2/K-A1 ratio 0.50000
Scanning mode: continuous from 3° to 55° (Bragg's angle 2 theta)
Step [°2Th.] 0.0170
Step duration [s] 35.5301
Starting angle [°2Th.] 3.0034
Finishing angle [°2Th.] 54.9894
Rotation: yes The X-ray powder diffraction diagrams obtained for Examples 1 and 2 are shown in FIGS. 1 and 3.

The invention claimed is:

1. A Crystalline form of co-crystals of agomelatine and p-toluenesulphonic acid of formula (I):

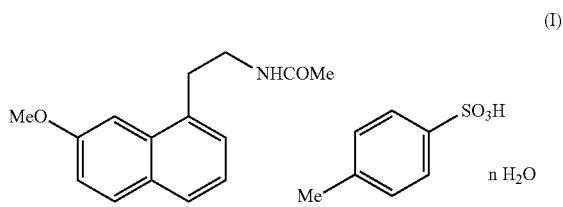

(I)

wherein n represents 0 or 1.

2. The crystalline form according to claim 1, which is the co-crystal of agomelatine and p-toluenesulphonic acid monohydrate, having the following X-ray powder diffraction diagram expressed in terms of interplanar distance d, Bragg's angle 2 theta (expressed in °±0.2), and relative intensity:

| 2-Theta (°) exp. | d (Å) exp. | Intensity (%) |
|---|---|---|
| 6.9631 | 12.6846 | 77.52 |
| 9.4831 | 9.31871 | 16.21 |
| 12.8823 | 6.86648 | 100 |
| 13.9527 | 6.34201 | 23.16 |
| 14.1761 | 6.24258 | 16.06 |

-continued

| 2-Theta (°) exp. | d (Å) exp. | Intensity (%) |
|---|---|---|
| 15.1817 | 5.83128 | 13.38 |
| 15.379 | 5.75689 | 25 |
| 15.5788 | 5.68351 | 46.24 |
| 16.7156 | 5.29947 | 94.46 |
| 17.2926 | 5.12391 | 37.98 |
| 18.4671 | 4.80058 | 92.47 |
| 18.6356 | 4.75756 | 22.34 |
| 19.199 | 4.6192 | 25.69 |
| 19.6747 | 4.50857 | 35.74 |
| 20.1398 | 4.4055 | 28.53 |
| 21.6248 | 4.1062 | 14.93 |
| 22.0586 | 4.02643 | 52.23 |
| 22.2859 | 3.98587 | 99.09 |
| 23.2175 | 3.82799 | 15.22 |
| 23.9607 | 3.71092 | 32.37 |
| 25.1733 | 3.53485 | 42.09 |
| 26.0152 | 3.42233 | 16.64 |
| 27.7148 | 3.2162 | 39.29 |
| 28.23 | 3.15866 | 11.25 |
| 28.4033 | 3.13979 | 16.33 | including the forms whose diffraction angles correspond to within ±0.2°.

3. The crystalline form according to claim 1, which is the co-crystal of agomelatine and p-toluenesulphonic acid, having the following X-ray powder diffraction diagram expressed in terms of interplanar distance d, Bragg's angle 2 theta (expressed in °±0.2), and relative intensity:

| 2-Theta (°) exp. | d (Å) exp. | Intensity (%) |
|---|---|---|
| 11.2964 | 7.82664 | 21.53 |
| 11.6596 | 7.58367 | 20.45 |
| 13.4436 | 6.58103 | 61.31 |
| 15.2416 | 5.80848 | 18.42 |
| 16.0185 | 5.52847 | 30.89 |
| 17.3473 | 5.10789 | 41.39 |
| 17.8289 | 4.97096 | 54.3 |
| 18.2535 | 4.85629 | 100 |
| 20.4891 | 4.33118 | 19.84 |
| 20.6912 | 4.28932 | 45.12 |
| 20.9516 | 4.23659 | 36.73 |
| 21.3088 | 4.16638 | 14.93 |
| 22.2998 | 3.98342 | 33.92 |

-continued

| 2-Theta (°) exp. | d (Å) exp. | Intensity (%) |
|---|---|---|
| 23.129 | 3.84244 | 24.66 |
| 23.4107 | 3.79685 | 12.89 |
| 23.6474 | 3.75938 | 12.34 |
| 23.9983 | 3.7052 | 12.8 | including the forms whose diffraction angles correspond to within ±0.2°.

4. A process for obtaining the co-crystals of agomelatine and p-toluenesulphonic acid according to claim 1, wherein:
   agomelatine and p-toluenesulphonic acid monohydrate are mixed in an organic or aqueous-organic solvent in the desired proportions;
   the solution obtained is stirred and optionally heated at a temperature not greater than the boiling point of the chosen solvent;
   the mixture is cooled, with stirring, and the complex precipitates naturally or precipitates after being taken up in a second solvent;
   the precipitate obtained is filtered and dried;
   optionally, the precipitate is dried by heating.

5. A process for the preparation of the co-crystals of agomelatine and p-toluenesulphonic acid according to claim 1, wherein the two constituents are co-ground.

6. A process for the preparation of the co-crystals of agomelatine and p-toluenesulphonic acid according to claim 1, wherein the two constituents are mixed in an organic or aqueous-organic solvent and then frozen and dried at a very low temperature.

7. A process for the preparation of the co-crystals of agomelatine and p-toluenesulphonic acid according to claim 1, wherein the powders of agomelatine and the acid in question are mixed in a mixer and the mixture is then extruded by twin-screw extrusion without a die in order to obtain a solid grain directly at the outlet of the extruder.

8. A pharmaceutical composition comprising as active ingredient the co-crystals of agomelatine and p-toluenesulphonic acid according to claim 1, in combination with one or more inert, non-toxic, pharmaceutically acceptable carriers.

\* \* \* \* \*